United States Patent [19]

Nakayama et al.

[11] Patent Number: 5,383,468
[45] Date of Patent: Jan. 24, 1995

[54] CARDIAC OUTPUT AND RIGHT VENTRICULAR EJECTION FRACTION SYSTEM

[75] Inventors: Tadashi Nakayama; Kohei Ono; Shinji Yamamori; Hidehiro Hosaka; Yoji Sato; Shiniti Shioya, all of Tokyo; Takasuke Imai, Gunma, all of Japan

[73] Assignee: Nihon Kohden Corporation, Tokyo, Japan

[21] Appl. No.: 783,930

[22] Filed: Oct. 29, 1991

[30] Foreign Application Priority Data

Oct. 31, 1990 [JP] Japan ................................ 2-295044

[51] Int. Cl.$^6$ ............................................. A61B 5/029
[52] U.S. Cl. ................................. 128/713; 128/692; 128/736
[58] Field of Search ....................... 128/691.4, 713, 736

[56] References Cited

U.S. PATENT DOCUMENTS

| | | | |
|---|---|---|---|
| 4,718,423 | 1/1988 | Willis et al. | 128/634 |
| 4,817,624 | 4/1989 | Newbower | 128/713 X |
| 4,856,530 | 8/1989 | Vandervelden | 128/692 |
| 4,858,618 | 8/1989 | Konno et al. | 128/713 |
| 4,911,174 | 3/1990 | Pederson et al. | 128/694 X |

*Primary Examiner*—Angela D. Sykes
*Attorney, Agent, or Firm*—Sughrue, Mion, Zinn, Macpeak & Seas

[57] ABSTRACT

A cardiac output and right ventricular ejection fraction computer comprises a catheter, having an indicator injection port which is located at the right ventricular, inserted into an intravascular of a patient and retained therein; thermal detector device, mounted on a distal portion of the catheter, for detecting the temperature of blood ejected from the right ventricle; signal processor device for calculating the right ventricular ejection fraction from a thermodilution curve obtained by detecting variation of the blood temperature measured by the thermal detector device when a indicator is injected into the right ventricular through the catheter; data input device for inputting data to the signal processor device.

3 Claims, 7 Drawing Sheets

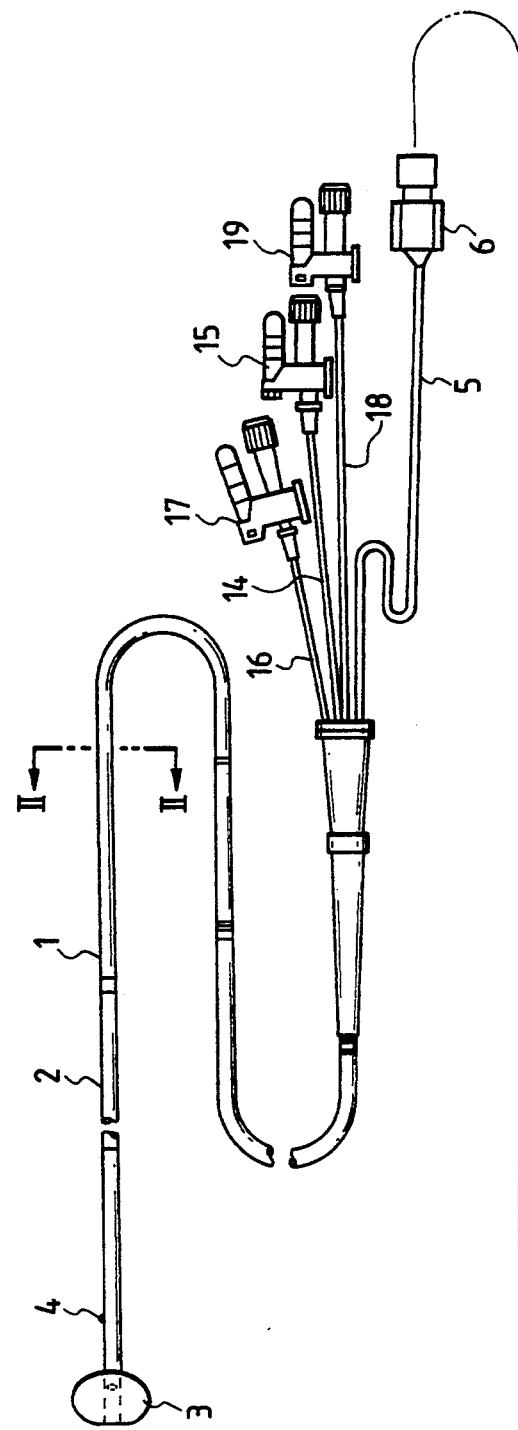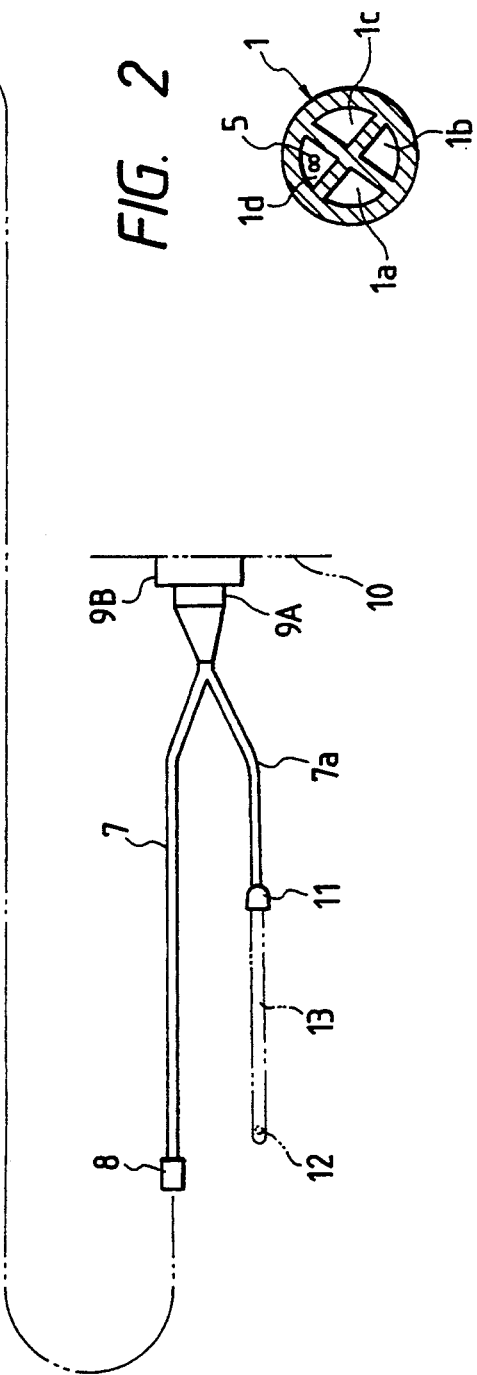

RESULT
CO : 5.00 L/min
CI : 2.94 L/min/m×m
SV : 62.5 mL
SI : 36.8 mL/m×m

EF : 60.8 %
EDV : 103 mL
EDVI : 60.6 mL/m×m

EF1 : 53.4   EF2 : 48.4

CONDITION
HR : 80 bpm
Tb : 37.0 °C
Ti : 0.0 °C
HT : 170 cm
WT : 60 kg
CC : .542
CL : 60 cm
BSA : 1.70 m×m

EF3 : 40.5

$$EF1 = 1 - \frac{B+b}{A+a} \qquad EF1_{corr} = 1 - \frac{B}{A}$$

CARDIAC OUTPUT AND RIGHT VENTRICULAR EJECTION FRACTION SYSTEM

BACKGROUND OF THE INVENTION

The invention relates to a cardiac output and right ventricular ejection fraction computer which measures a cardiac output, a right ventricular ejection fraction, and a right ventricular end-diastolic volume which are the subjects of hemodynamic study.

Methods of measuring the right ventricular ejection fraction in the hemodynamic study which have heretofore been known include: RI angiography, X-ray angiography, ultrasonic echocardiography, and an indicator dilution method.

The RI angiography measures the right ventricular ejection fraction by injecting a radioisotope into the body and it exhibits a high degree of measurement accuracy. However, measurement must be made within an IR administration area, which makes the method somewhat cumbersome. In addition, the method does not allow frequent measurements, giving consideration to the influence of the injected radioisotope on the body.

The X-ray angiography and the ultrasonic echocardiography are methods for calculating the right ventricular ejection fraction through image analysis. In measurements based on these methods the form of, e.g., the left ventricle can be approximated as an ellipse of revolution, while the form of the right ventricle cannot be approximated due to its anatomic complexities.

The indicator dilution method, particularly, a thermodilution method, measures the right ventricular ejection fraction by leaving a thermodilution catheter in the body when making a measurement by right ventricular catheterization. Thus, the measurement is relatively simple and easy. In the calculation of the right ventricular ejection fraction by the thermodilution method, a plateau method and an exponential method are known.

The plateau method calculates the ejection fraction from differences between four successive end-diastolic plateaus produced in the decay line of a thermodilution curve and a base line, measures the ejection fractions over four beats, and averages the three calculated ejection fractions to obtain the ejection fraction of the thermodilution curve.

The exponential method synchronizes an R wave of an ECG with the plateaus produced in the decay line of a thermodilution curve, derives an exponential function from the decay curve of the thermodilution curve, and calculates a Lime constant of this measuring system to obtain the ejection fraction.

By the way, to calculate the right ventricular ejection fraction by the plateau method in a thermodilution method-based measurement, the larger the ejection fraction is, the greater errors the ejection fractions calculated every ejection exhibit. As a result, the calculated average of four ejections becomes smaller than the actual value.

This error is caused by the fact that substantially 0° C.-cold water consisting of physiological saline or 5% dextran used as an indicator (injectate) remains within the catheter and that the vessel wall and myocardiac wall are cooled through the catheter wall. Therefore, it is the catheter insert length that determines the degree of an error. This can be said from the result of the investigation of a model that the ejection fraction obtained from a thermodilution curve that is measured by directly injecting an indicator from the right ventricle of the model exhibited no error.

As shown in FIG. 10, (a) shows an exemplary thermodilution curve when the catheter insert length is 90 cm, while (b) shows a thermodilution curve in which only the influence of the catheter in cooling the vessel wall and myocardiac wall is plotted.

In FIG. 10, let it be assumed that temperature variations caused by cold injectate in four beats are A, B, C, D, and that temperature variations caused by a negative heat produced by the injectate remaining in the catheter through the catheter wall that remains within the body are a, b, c, d. In addition, when $$A' = A + a \quad B' = B + b$$

$$C' = C + c \quad D' = D + d$$

ejection fractions $EF_1$, $EF_2$, $EF_3$ each ejection are conventionally calculated as:

$$EF_1 = 1 - B'/A'$$

$$EF_2 = 1 - C'/B'$$

$$EF_2 = 1 - D'/C'$$

Errors resulting because the influence of the catheter in cooling the vessel wall and myocardiac wall was not considered.

The invention has been proposed to overcome the above problems and has as an object the provision of a cardiac output and right ventricular ejection fraction system which is capable of correcting the influence of the catheter in cooling the vessel wall and myocardiac wall and of implementing highly accurate measurement when measuring ejection fractions and the like while calculating the thermodilution curve by the plateau method, the thermodilution curve being obtained by the thermodilution method.

SUMMARY OF THE INVENTION

To achieve the above object, the invention is applied to a cardiac output and right ventricular ejection fraction system that includes: a catheter which is inserted into the body of a patient and retained therein so that its indicator injection port is located at the right ventricle; a thermal detector, which is mounted on a distal of the catheter, for detecting the temperature of blood ejected from the right ventricle; a signal processor for calculating a right ventricular ejection fraction from a thermodilution curve obtained by detecting variations of a blood temperature measured by the thermal detector when a cold indicator is injected into the right ventricle through the catheter; and data input means which inputs a catheter insert length to the signal processor. In such a system, the signal processor calculates the right ventricular ejection fraction by correcting a measurement error attributable to the catheter insert length.

The longer the catheter insert length is, the greater the influence of the catheter in cooling the vessel wall and myocardiac wall becomes. The above construction can calculate the right ventricular ejection fraction while correcting measurement errors attributable to the catheter insert length.

An aspect of the present invention is to provide a cardiac output and right ventricular ejection fraction system including a catheter which is inserted into the body of a patient and retained therein so that an indicator injection port thereof is located at the right ventricle; a thermal detector, mounted on a distal of the catheter, for detecting the temperature of blood ejected from the right ventricle; a signal processor for calculating a right ventricular ejection fraction from a thermodilution curve obtained by detecting variations of a blood temperature measured by the thermal detector when a cold indicator is injected into the right ventricle through the catheter; and data input means for inputting a catheter insert length to the signal processor; wherein the signal processor calculates the right ventricular ejection fraction by correcting a measurement error attributable to the catheter insert length.

BRIEF DESCRIPTION OF THE DRAWINGS

FIG. 1 is a plan view showing a catheter of and connection cords of the present invention used in hemodynamic study;

FIG. 2 is a sectional view taken along a line II—II shown in FIG. 1;

DETAILED DESCRIPTION OF THE PREFERRED EMBODIMENTS

An embodiment of the invention will be described in detail with reference to the drawings.

FIG. 1 shows a thermodilution catheter for hemodynamic measurement.

Figure 5:
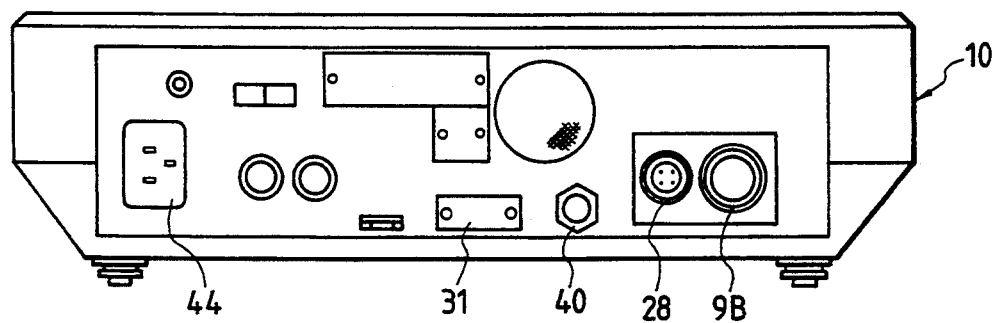
FIG. 5 is a rear view of the computer shown in FIG. 3.

In FIG. 1, an injection port 2 is provided on the side of the distal of a catheter 1, the injection port 2 serving to inject an indicator to the right ventricle. On its distal are a balloon 3 and a thermistor 4 whose thermal response time is as short as, e.g., 200 msec. A catheter connection cord 7 is connected to a thermistor connector 6 through a connector 8, the connector 6 being attached to a signal cable 5 that extends to the proximal side of the catheter 1. A connector 9A disposed on the proximal side of the connection cord 7 is connected to a catheter connection connector 9B arranged on the back of a computer body 10 (see FIG. 5). A temperature measuring probe 13 is connected to a connector 11 of a connection cord 7a, the probe 13 carrying a thermistor 12 for measuring the temperature of an injectate.

An indicator is injected from a termination device 15 for injection attached to a tube 14 that extends toward the proximal side of the catheter 1. The indicator is cooled to 0° C. A termination device 17 for pulmonary arterial pressure is attached to the proximal side of a tube 16, while a termination device 19 for the balloon is attached to the proximal side of a tube 18. Here, the tubes 14, 16, 18 communicate with passages 1a, 1b, 1c inside the catheter 1, respectively (see FIG. 2), and the signal cable 5 to be connected to the thermistor 4 is inserted through a passage 1d inside the catheter 1.

Figure 3:
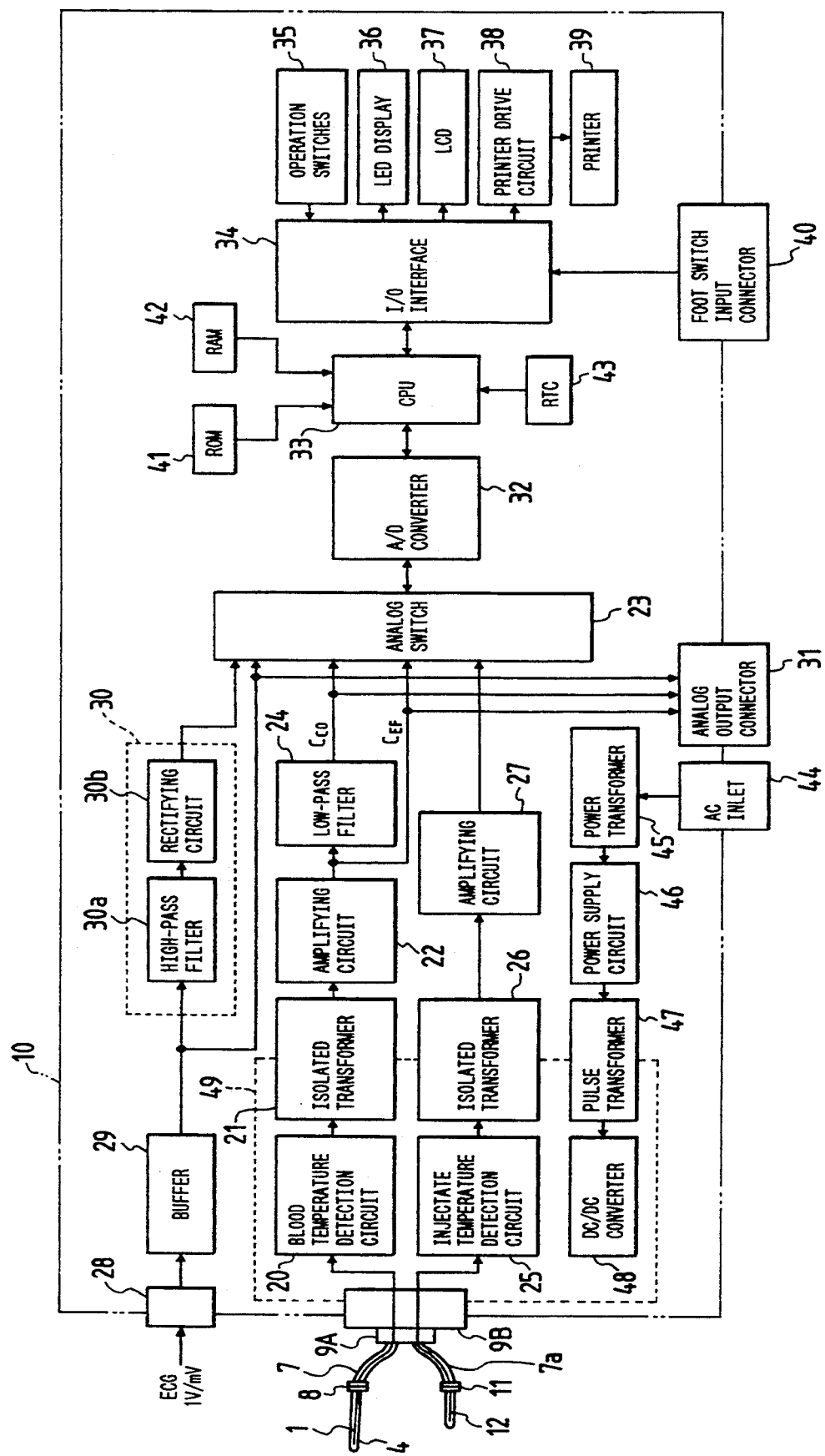
FIG. 3 is a block diagram showing an embodiment of a cardiac output and right ventricular ejection fraction computer of the present invention.

FIG. 3 is a block diagram of a cardiac output and right ventricular ejection fraction system of the invention.

In FIG. 3, a blood temperature that is detected by the thermistor 4 mounted on the catheter 1 is read out as a thermodilution signal in the form of a voltage at a blood temperature detection circuit 20. This thermodilution signal is first amplified by an amplifying circuit 22 through an isolated transformer 21, and then not only supplied to an analog switch 23 as a thermodilution signal $C_{EF}$, but also fed to a low-pass filter 24. At the low-pass filter 24, a step thermodilution signal is converted into a thermodilution signal $C_{CO}$ for cardiac output calculation, and the thus converted signal is applied to the analog switch 23.

Also, the injectate temperature detected by the thermistor 12 is read out as a thermodilution signal in the form of voltage at an injectate temperature detection circuit 25, and this thermodilution signal is amplified at an amplifying circuit 27 through an isolated transformer 26, and fed to the analog switch 23.

An electrocardiographic signal ECG, amplified to about 1 V, is received by a monitor TV from an ECG input connector 28, and the signal ECG is then not only fed to the analog switch 23 through a buffer 29, but also outputted to a high-pass filter 30a. The high-pass filter 30a and a subsequent rectifying circuit 30b constitute a synchronizing signal generating circuit 30, which generates a synchronizing signal for detecting plateaus of a thermodilution signal for ejection fraction calculation from the electrocardiographic signal fed from the buffer 29. The generated synchronizing signal is supplied to the analog switch 23.

The ECG signal outputted from the buffer 29 and the thermodilution signal outputted from the amplifying circuit. 22 and the low-pass filter 24 can be taken out to an external terminal from an analog output connector 31.

The analog switch 23 sequentially selects one of the inputted analog signals and outputs the selected signal to an A/D converter 32. A digital signal converted at the A/D converter 32 is read out by a central processing unit (CPU) 33.

Figure 4:
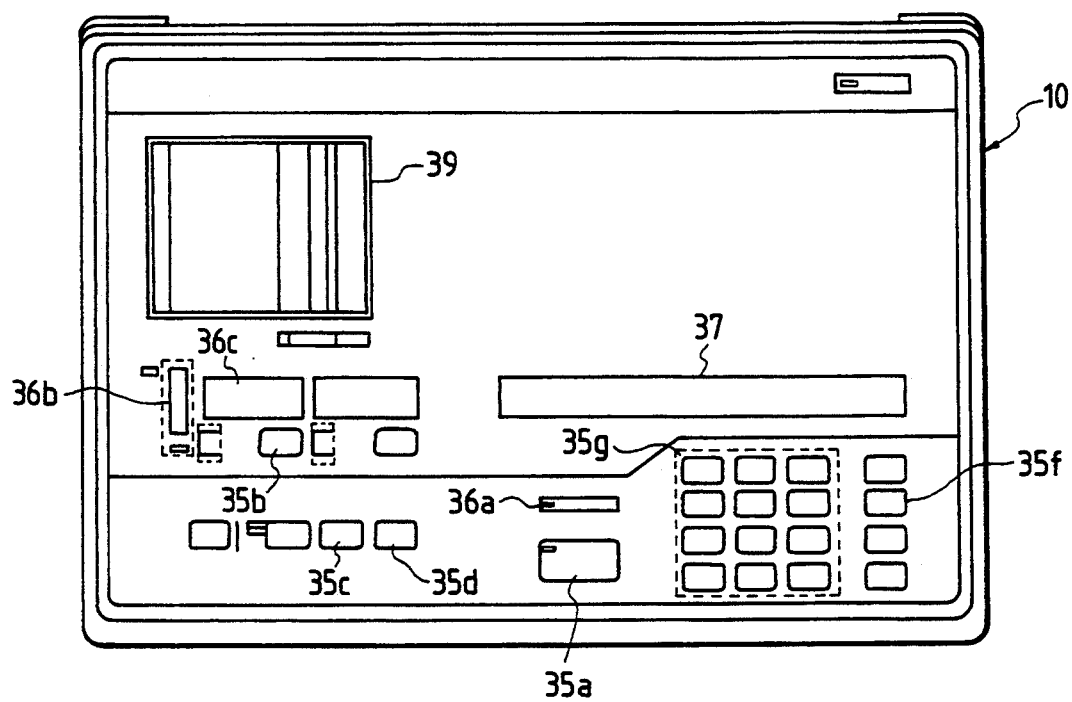
FIG. 4 is a plan view of the computer shown in FIG. 3.

Connected to an input/output interface 34 that is controlled by the CPU 33 are: a group of operation switches 35 which serve to operate the start and end of a measurement, enter patient data, switch screens, operate the start and stop of a printing operation by a printer; a light-emitting diode display (LED display) 36 and a liquid crystal display (LCD) 37 both displaying calculation results and patient data; and a printer drive circuit 38 (see FIG. 4). The printer drive circuit 38 drives a printer 39 to print out measurement results and the like. A foot switch is connected to an input connector 40 that is connected to the I/O interface 34.

Patient data such as a catheter insert length is entered by first pressing a patient data input key 35f and then operating a ten-key pad 35g, and each input data is displayed on the LCD 37 upon entry. The patient data input key 35f and the ten-key pad 35g constitute input means.

A ROM (read only memory) 41 stores programs for operational procedure and calculation, while a RAM (random access memory) 42 stores measurement data and the like, both being connected to the CPU 33. An RTC (realtime clock) 43 is connected to the CPU 33.

The RTC outputs a block signal necessary for signal processing.

An AC power supply from an AC inlet 44 is transformed by a power supply transformer 45, rectified to a DC power supply by a power supply circuit 46, and supplied to a DC/DC converter 48 through a pulse transformer 47. Direct current power outputted from the DC/DC converter 48 is fed to the blood temperature detection circuit 20 and the injectate temperature detection circuit 25 which are in an isolation circuit 49.

Figure 6:
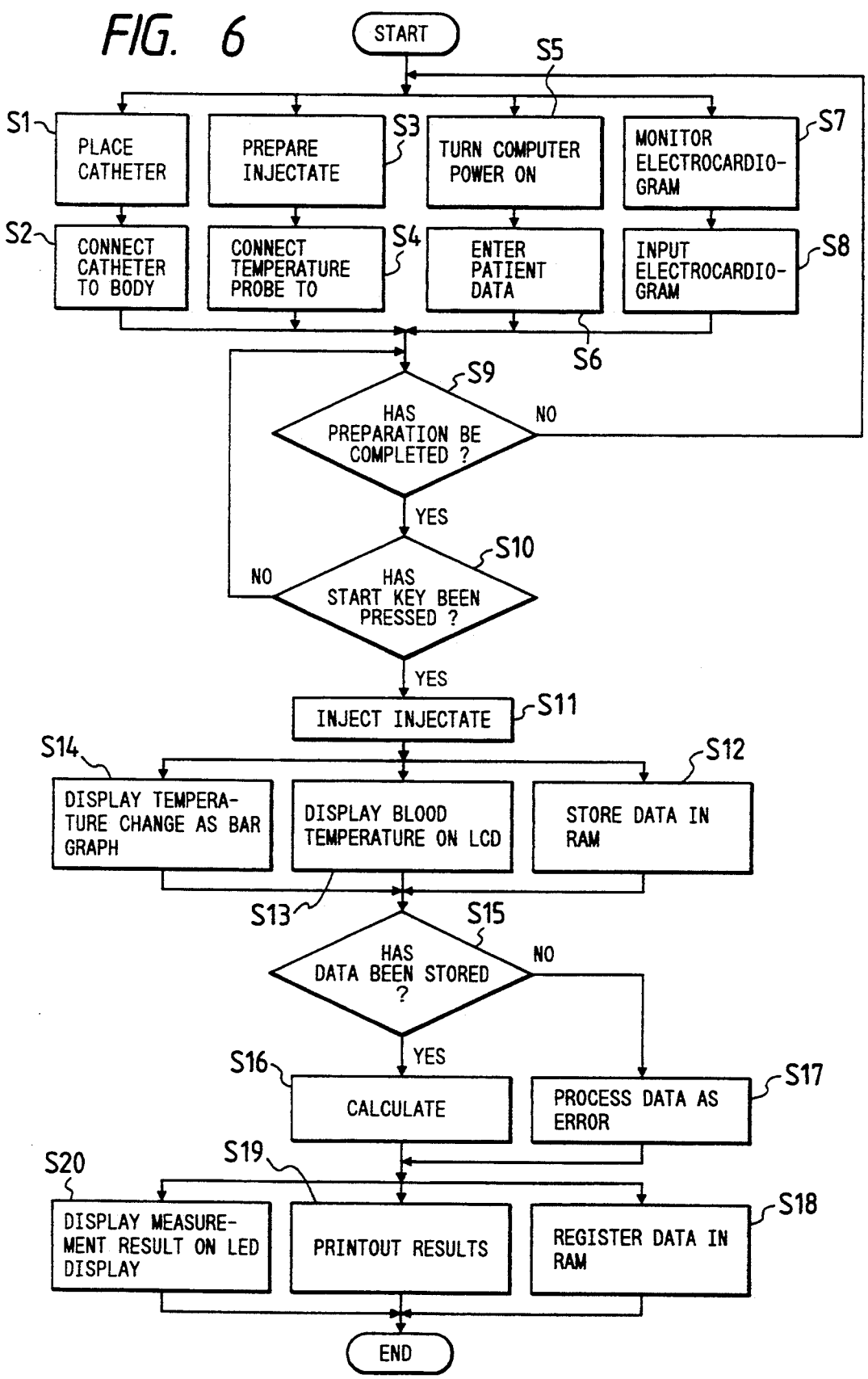
FIG. 6 is an operational flow chart showing a measurement procedure.

An operation of the thus constructed cardiac output and right ventricular ejection fraction system will be described with reference to an operational flow chart shown in FIG. 6.

First, the catheter 1 is placed so that its distal portion is located at the pulmonary artery of a patient and that its injection port 2 is located at his or her right ventricle. Then, the catheter 1 is connected to the system body 10 through the connection cord 7 (Steps S1 and S2).

The indicator (injectate) is prepared and the temperature measuring probe 13 is connected to the computer body 10 (Steps S3 and S4).

The power of the system body 10 is turned on, and patient data such as the height and weight of the patient to calculate his or her body surface area, a catheter constant to calculate the cardiac output, a catheter insert length to calculate the ejection fraction, and the like are entered through the ten-key pad 35g of the data input means (Steps S5 and S6).

An ECG of the patient is monitored to input an electrocardiographic signal ECG to the system (Steps S7 and S8).

Upon completion of all the preparation, a measurement preparation completion lamp 36a is lit up (Step S9). A measurement start key 35a is pressed signalled by the lighting up of the lamp 36a, and the 0° C. indicator is injected into the patient from the injection termination device 15 in quantities of about 5 to 10 ml at a stretch (Steps S10 and S11).

Figure 7:
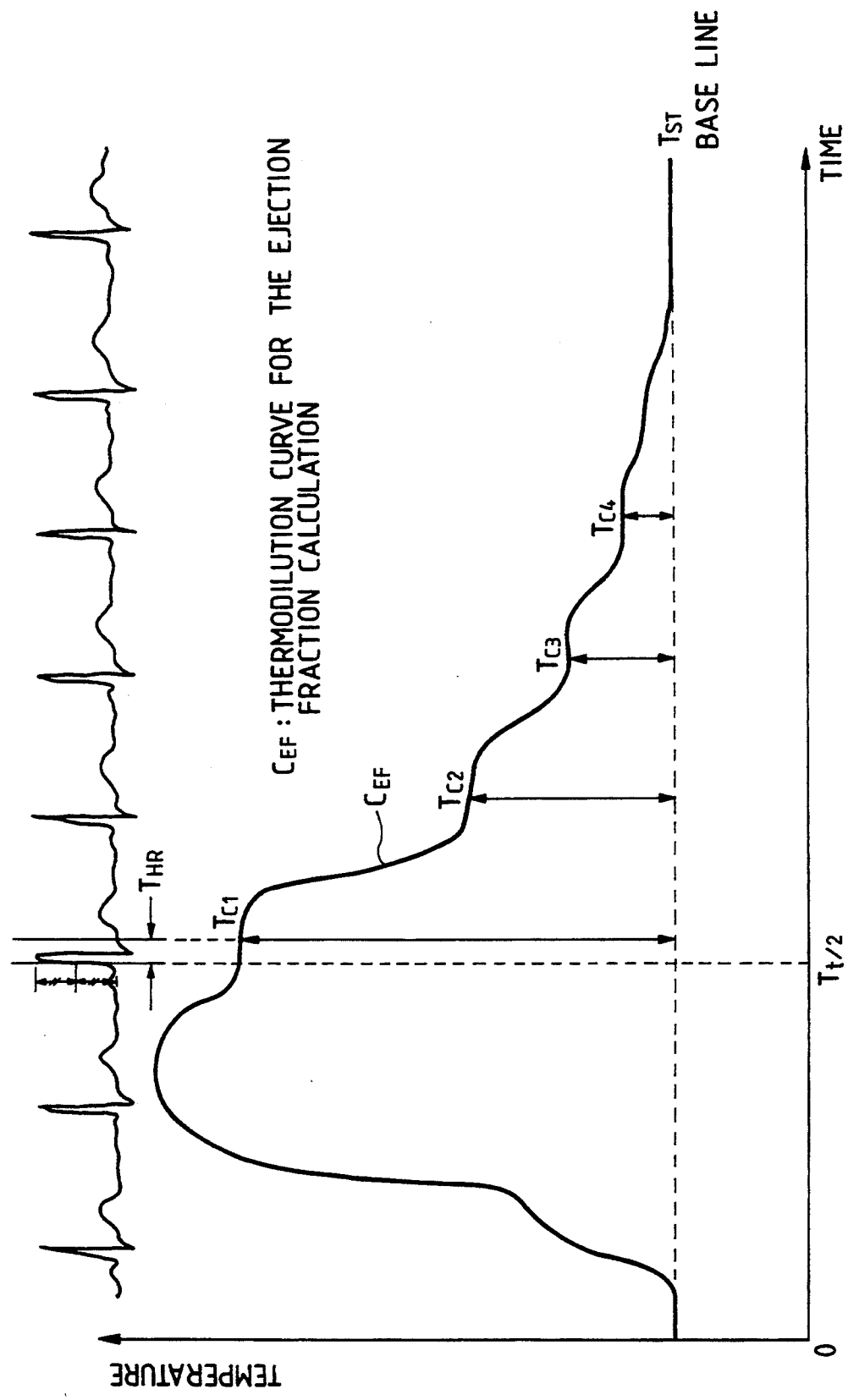
FIG. 7 is a waveform chart illustrative of the measurement of an ejection fraction.

Subsequent to this operation starts the reading of a thermodilution signal $C_{CO}$ for cardiac output measurement a thermodilution signal $C_{EF}$ for ejection fraction measurement, and an electrocardiographic signal ECG. After A/D converted, each signal is stored in the RAM 42. The reading of the signal data can be confirmed by the turning on of a thermodilution curve display 36b. With respect to the injectate temperature, the smallest value obtained between the start and end of a measurement is stored in the RAM 42. In addition thereto, a heart rate $HR_{ST}$ at the measurement start is stored in the RAM 42, as well as a first value of a thermodilution curve for ejection fraction calculation is stored in the RAM 42 as a base line $T_{ST}$. Plateaus are recognized in the following way. As shown in FIG. 7, with a value half the peak of a QRS wave of an ECG in any past three seconds as a threshold, a time delay ($T_{HR}$: 50 to 300 msec) is varied by the heart rate $HR_{ST}$ defined at the measurement start as from a timing $T_{t/2}$ that is a timing exceeding the threshold, and the largest four thermodilution signals $T_{Cn}$ ($T_{C1}$, $T_{C2}$, $T_{C3}$, $T_{C4}$) during such variation are detected. These values are stored in the RAM 42. Used as detection points are those in the range of 10 to 85% of the maximum value in the decay line of a thermodilution signal $C_{EF}$. These operations correspond to Step S12.

The blood temperature is displayed on the LCD 37 and its temperature variations are expressed in the form of a bar graph (Steps S13 and S14).

Figure 8:
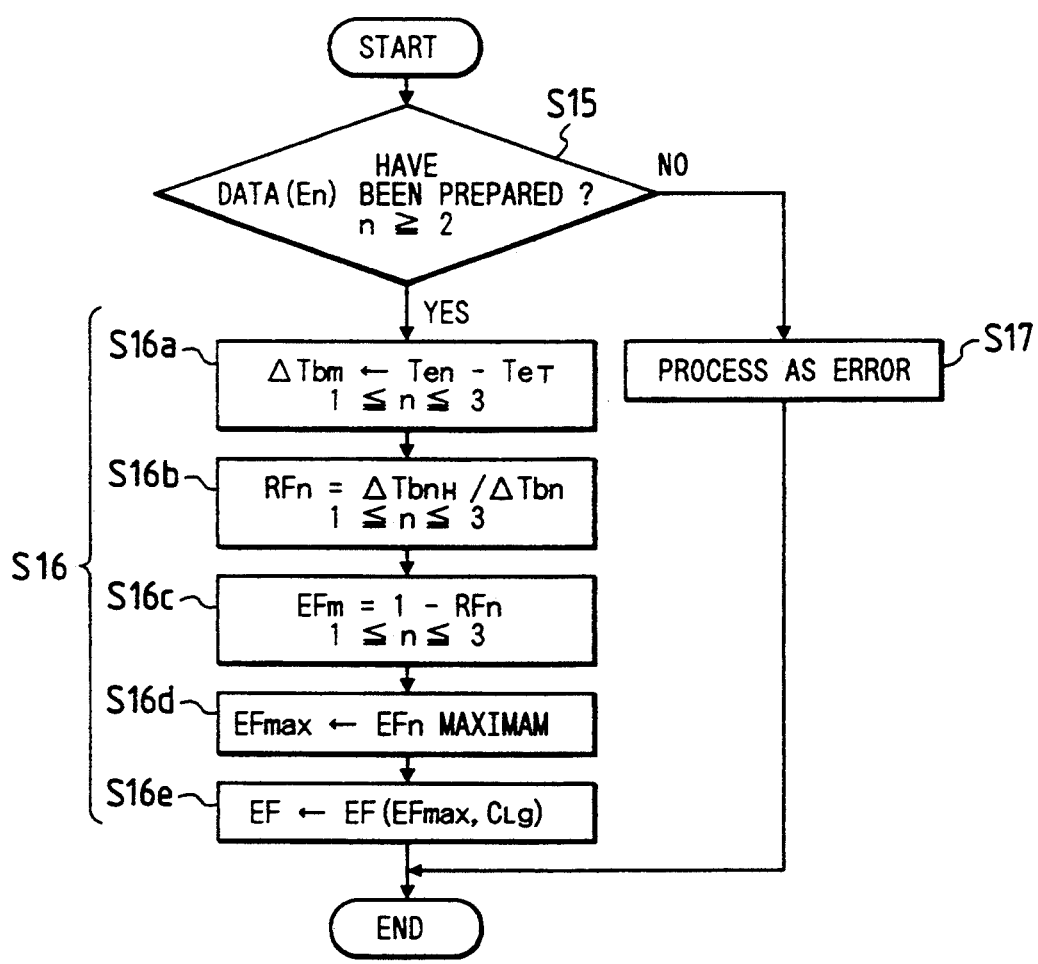
FIG. 8 is an operational flow chart showing an ejection fraction calculation routine.

Once all the data have been prepared, the operation of calculating the ejection fraction based on a calculation routine shown in FIG. 8 is performed (Steps S15 and S16).

First, a base line value $T_{ST}$ is subtracted from each plateau value $T_{Cn}$ of a detected thermodilution curve (Step S16a).

Then, the operation of dividing the difference $\Delta T_{bn+1}$ by the difference $\Delta T_{bn}$ is repeated to obtain three quotients $RF_n$ (Step S16b).

Successively, each quotient $RF_n$ is subtracted from 1 to obtain ejection fractions $EF_n$ (Step S16c).

The maximum $EF_{max}$ is selected from among the calculated ejection fractions $EF_n$ ($EF_1$, $ER_2$, $ER_3$), and the maximum $EF_{max}$ is then subjected to a catheter insert length $C_{LG}$ correcting process to obtain the right ventricular ejection fraction EF (Steps S16d and S16e). Here, it is well known that it is the maximum value that is less erroneous among the three ejection fractions derived from the thermodilution curve.

In the case where no thermodilution signal $T_{Cn}$ data are prepared, the operation is processed as an error (Step S17).

The above calculations may be expressed by the following equations.

$$EF_1 = 1-(T_{C2}-T_{ST})/(T_{C1}-T_{ST})$$

$$EF_2 = 1-(T_{C3}-T_{ST})/(T_{C2}-T_{ST})$$

$$EF_3 = 1-(T_{C4}-T_{ST})/(T_{C3}-T_{ST})$$

$$EF = EF_{max}/(1-K_{corr} \times 10^{-3} \cdot C_{LG})$$

where $K_{corr}$ is a correct constant that takes values ranging from 2.00 to 3.00 cm$^{-1}$, and is varied with changes in the material and size of the catheter 1; and $C_{LG}$ is the catheter 1 insert length to the injection port 2.

To obtain the cardiac output CO, the thermodilution signal $C_{CO}$ is calculated by the formulas by Stewart-Hamilton.

The stroke volume SV is calculated by dividing the cardiac output CO by the heart rate HR.

The right ventricular end-diastolic volume RVEDV is calculated by dividing the stroke volume SV by the right ventricular ejection fraction RVEF.

A stroke volume index SI and an end-diastolic volume index RVEDVI are obtained by standardizing while dividing the stroke volume SV and the right ventricular end-diastolic volume RVEDV by the body surface area BSA, respectively.

The above calculations may be expressed by the following equations.

$$SV = CO/HR_{ST} \quad SI = SV/BSA$$

$$RVEDV = SV/RVEF \quad RVEDVI = RVEDV/BSA$$

Upon completion of all the measurements, the measured data are registered in the RAM 42 (Step S18).

Figure 9:
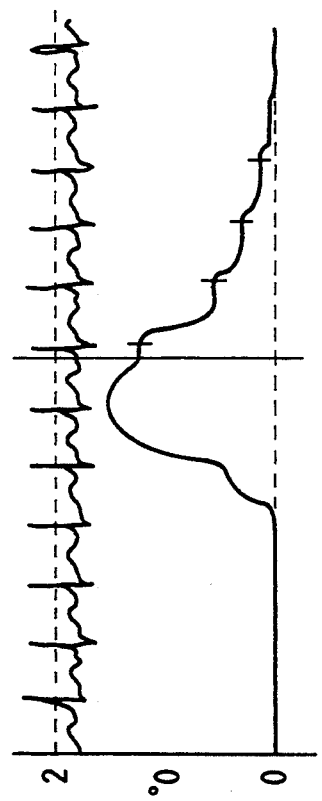
FIG. 9 is a diagram showing an exemplary printout of a measurement result.
Figure 10:
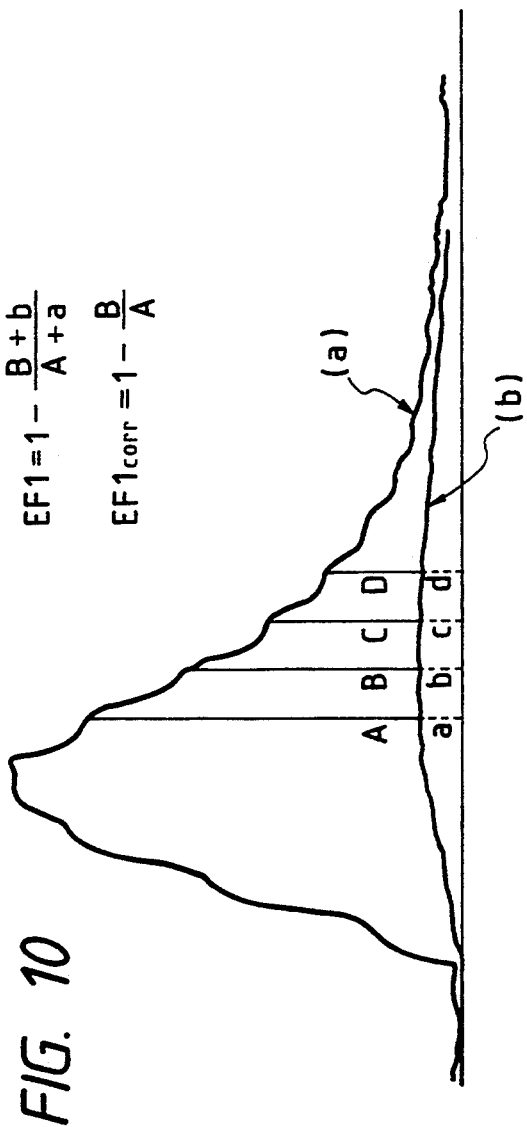
FIG. 10 is a waveform chart illustrative of generation of measurement errors.

After the end of the measurements, the right ventricular ejection fraction and the right ventricular end-diastolic volume are respectively displayed on the LED display 36c by operating the display switch key 35b. When the measurement result print key 35c has been pressed, the measurement results and the measured waveforms are printed as shown in an exemplary printout of FIG. 9. By pressing a list print key 35d, the measurement results and the averages for the latest 5 measurements are printed out.

When the ejection fraction display key 35e has been pressed, the three ejection fractions detected every ejection are displayed on the LCD 37 (Steps S19 and S20).

When the cardiac output is calculated using the Edwards formula based on a step waveform such as the thermodilution signal $C_{EF}$ for ejection fraction calculation, it is empirically known that the calculated results are erratic. However, the system of the invention uses the thermodilution signal $C_{EF}$ that has passed through the low-pass filter 24 whose time constant is about the same as that of an ordinary thermodilution catheter 1, analyzes such filter output as the thermodilution signal $C_{CO}$ for cardiac output calculation, and calculates the cardiac output, thereby allowing stable measurement to be implemented.

As described in the foregoing, the invention can correct errors attributable to the influence of a cold indicator remaining within the catheter which cools the vessel wall and myocardiac wall. Therefore, the cardiac output, the right ventricular ejection fraction, and the right ventricular end-diastolic volume can be measured highly accurately and easily.

What is claimed is:

1. A cardiac output and right ventricular ejection fraction system comprising:

a catheter, having an indicator injection portion which is located at the right ventricle, adapted to be inserted intravascularly into a patient and retained therein;

thermal detector means, mounted on a distal portion of said catheter, for detecting the temperature of blood ejected from said right ventricle;

signal processor means for calculating said right ventricular ejection fraction from a thermodilution curve obtained by detecting variation of said blood temperature measured by said thermal detector means when an indicator is inserted into the right ventricle through said catheter; and data input means for inputting data to said signal processor means;

wherein said data includes an insert length of said catheter.

2. A cardiac output and right ventricular ejection fraction system comprising:

a catheter, having an indicator insection port which is located at the right ventricle, adapted to be inserted intravascularly into a patient and retained therein;

thermal detector means, mounted on a distal portion of said catheter, for detecting the temperature of blood ejected from said right ventricle, signal processor means for calculating said right ventricular ejection fraction from a thermodilution curve obtained by detecting variation of said blood temperature measured by said thermal detector means when an indicator is inserted into the right ventricle through said catheter;

data input means for inputting data to said signal processor means;

wherein said data includes an insert length of said catheter; and wherein said signal processor means calculates said right ventricular ejection fraction by correcting a measurement error attributable to said insert length of said catheter.

3. A cardiac output and right ventricular ejection fraction system as claimed in claim 2, wherein said indicator injection port injects an indicator which is substantially 0° C. cold water including one of physiological saline and 5% dextran.

* * * * *